US012765853B2

(12) United States Patent
Joo et al.

(10) Patent No.: US 12,765,853 B2
(45) Date of Patent: Oct. 20, 2026

(54) MULTI-BONE DENSITY DISPLAY METHOD AND APPARATUS, COMPUTER-READABLE RECORDING MEDIUM, AND COMPUTER PROGRAM

(71) Applicant: OSSTEMIMPLANT CO., LTD., Seoul (KR)

(72) Inventors: Won Hyeong Joo, Incheon (KR); Su Hee Park, Gyeonggi-do (KR); Kyoo Ok Choi, Seoul (KR)

(73) Assignee: OSSTEMIMPLANT CO., LTD., Seoul (KR)

( * ) Notice: Subject to any disclaimer, the term of this patent is extended or adjusted under 35 U.S.C. 154(b) by 439 days.

(21) Appl. No.: 18/286,189

(22) PCT Filed: May 10, 2022

(86) PCT No.: PCT/KR2022/006600
§ 371 (c)(1),
(2) Date: Oct. 9, 2023

(87) PCT Pub. No.: WO2022/240106
PCT Pub. Date: Nov. 17, 2022

(65) Prior Publication Data
US 2024/0374228 A1 Nov. 14, 2024

(30) Foreign Application Priority Data
May 10, 2021 (KR) ........................ 10-2021-0059925

(51) Int. Cl.
*A61B 6/51* (2024.01)
*A61B 6/46* (2024.01)
*A61B 34/10* (2016.01)

(52) U.S. Cl.
CPC ................ *A61B 6/51* (2024.01); *A61B 6/463* (2013.01); *A61B 34/10* (2016.02); *A61B 2034/107* (2016.02)

(58) Field of Classification Search
CPC ........... A61B 6/51; A61B 6/463; A61B 34/10; A61B 2034/107; A61B 2034/101;
(Continued)

(56) References Cited

U.S. PATENT DOCUMENTS 6,224,373 B1 * 5/2001 Lee ........................ A61B 6/506 433/172
8,644,568 B1 * 2/2014 Hoffmann .............. G16H 50/50 382/128

(Continued)

FOREIGN PATENT DOCUMENTS

CN 210446984 U 5/2020
KR 1020000060352 A 10/2000

(Continued)

OTHER PUBLICATIONS

Vandeweghe et al., "Utilizing micro-computed tomography to evaluate bone structure surrounding dental implants: A comparison with histomorphometry", 2013 (Year: 2013).*

*Primary Examiner* — Adil Partap S Virk
(74) *Attorney, Agent, or Firm* — Downs Rachlin Martin PLLC

(57) ABSTRACT

A method of displaying multiple bone density performed in a multiple bone density display device when planning an implant procedure includes overlaying a bone density display area including an implant body placement area with a tooth area, displaying a bone density value corresponding to the bone density display area in a first color, and determining whether to display a second color on an edge of the implant body or an edge of the bone density display area displayed in the first color, based on a bone density difference value
(Continued)

between an area having a greatest bone density value and an area having a smallest bone density value in the bone density display area.
Embodiments have the effect of effective procedure planning by providing bone density information on an implant part when planning an implant procedure.

10 Claims, 13 Drawing Sheets

(58) Field of Classification Search
CPC ........ A61B 2034/102; A61B 2034/105; A61B 2090/365; A61B 6/032; A61B 6/5217; G16H 20/40; G16H 50/50
See application file for complete search history.

(56) References Cited

U.S. PATENT DOCUMENTS

2007/0167716 A1* 7/2007 Kinahan ................ A61B 6/032 600/407
2009/0263764 A1* 10/2009 Berckmans, III ...... A61B 6/032 433/215
2011/0045431 A1* 2/2011 Groscurth ................ A61C 9/00 433/74
2013/0004043 A1* 1/2013 Ross ..................... G06T 7/0016 382/128
2013/0101089 A1* 4/2013 Cho ..................... A61B 6/5241 378/62
2013/0196280 A1 8/2013 Kim et al.
2014/0133726 A1* 5/2014 Garner ................... A61B 6/032 382/131
2015/0310650 A1* 10/2015 Lu ...................... G01R 33/5608 324/322
2016/0058528 A1* 3/2016 Kim ..................... A61C 8/0015 427/2.27
2018/0322618 A1 11/2018 Smith
2018/0330501 A1* 11/2018 Muraoka ................ A61B 6/486
2022/0039868 A1* 2/2022 Chaoui .................. A61B 34/10
2022/0246269 A1* 8/2022 Choi ........................ A61B 6/51
2023/0093849 A1* 3/2023 Takahashi ................. G06T 5/50 382/128

FOREIGN PATENT DOCUMENTS

KR 101544773 B1 8/2015
KR 1020180038319 A 4/2018
KR 1020210008220 A 1/2021

* cited by examiner

MULTI-BONE DENSITY DISPLAY METHOD AND APPARATUS, COMPUTER-READABLE RECORDING MEDIUM, AND COMPUTER PROGRAM

TECHNICAL FIELD

Embodiments relate to a method of displaying a multiple bone density, and more particularly, to a method and apparatus for displaying a multiple bone density to plan an implant procedure.

BACKGROUND ART

People visit a dentist to treat teeth when having tooth decay or losing a tooth.

Dental treatments include a root canal, orthodontics, an implant, or other treatment methods. Among these, the implant refers to a replacement for replacing human tissue when the original human tissue is lost; however, in dentistry, it refers to the transplantation of an artificial tooth. The implant is a procedure to restore the function of a tooth by fixing an artificial tooth after placing an implant body made of titanium or other materials not rejected by a human body in the alveolar bone where a tooth was lost to replace a lost dental root.

The implant is a semi-permanent procedure, which may not damage surrounding dental tissue and may provide an artificial tooth having the almost same function and shape as a natural tooth.

The appropriateness of an overall procedure plan may need to be checked before performing a procedure by virtually selecting an artificial tooth and placing the selected artificial tooth in an expected implant position in advance through computer simulation of the implant procedure.

For example, to determine the position and type of an implant body and to plan a procedure, such as drilling, bone density information on an implant part may need to be checked.

Bone density has been typically displayed on an entire dental image screen, which renders the analysis of the bone density of an actually needed area difficult.

DISCLOSURE OF THE INVENTION

Technical Goals

To solve the problems described above, embodiments provide a method and apparatus for displaying multiple bone density to enable the effective checking of the bone density of an implant part when planning an implant procedure.

Technical Solutions

According to an embodiment, there is provided a method of displaying multiple bone density performed in a multiple bone density display device when planning an implant procedure including overlaying a bone density display area including an implant body placement area with a tooth area, displaying a bone density value corresponding to the bone density display area in a first color, and determining whether to display a second color on an edge of the implant body or an edge of the bone density display area displayed in the first color, based on a bone density difference value between an area having a greatest bone density value and an area having a smallest bone density value in the bone density display area.

The determining of whether to display the second color may include dividing the bone density display area into a plurality of areas in a longitudinal direction of the implant body, calculating the bone density difference value between the area having the greatest bone density value and the area having the smallest bone density value among the plurality of areas, and displaying the second color on the edge of the bone density display area when the bone density difference value is greater than or equal to a preset threshold value.

In the determining of whether to display the second color, the area having the greatest bone density value may include an area adjacent to a maxillary sinus or a mandibular sinus, and the area having the smallest bone density value may include an area adjacent to a tooth.

The displaying of the second color may include displaying the second color on the edge of the implant body when the bone density difference value is greater than or equal to a preset threshold value.

The displaying of the first color may include determining a bone density grade based on a bone density value of each pixel included in the implant body placement area and determining the first color according to the bone density grade, in which the bone density grade may include a first hard bone to a third hard bone, a first normal bone to a third normal bone, and a first soft bone to a third soft bone.

The implant body placement area may be automatically set based on implant body information including the length and diameter of the implant body.

In addition, according to another embodiment, there is provided a multiple bone density display device including a memory configured to store a control program for displaying multiple bone density and a processor configured to execute the control program stored in the memory, in which the processor is further configured to overlay a bone density display area including an implant body placement area with a tooth area, display a bone density value corresponding to the bone density display area in a first color, and determine whether to display a second color on an edge of the implant body or an edge of the bone density display area displayed in the first color, based on a bone density difference value between an area having a greatest bone density value and an area having a smallest bone density value in the bone density display area.

After displaying the bone density value in the first color, the processor may divide the bone density display area into a plurality of areas in a longitudinal direction of the implant body, may calculate the bone density difference value between the area having the greatest bone density value and the area having the smallest bone density value among the plurality of areas, and may display the second color on the edge of the bone density display area when the bone density difference value is greater than or equal to a preset threshold value.

The area having the greatest bone density value may include an area adjacent to a maxillary sinus or a mandibular sinus, and the area having the smallest bone density value may include an area adjacent to a tooth.

The processor may control to display the second color on the edge of the implant body when the bone density difference value is greater than or equal to the preset threshold value.

The processor may control the implant body placement area to be automatically set based on implant body information including the length and diameter of the implant body.

In addition, according to another embodiment, there is provided a computer-readable storage medium storing a computer program including instructions that, when executed by a processor, cause the processor to perform operations including overlaying a bone density display area including an implant body placement area with a tooth area, displaying a bone density value corresponding to the bone density display area in a first color, and determining whether to display a second color on an edge of the implant body or an edge of the bone density display area displayed in the first color, based on a bone density difference value between an area having a greatest bone density value and an area having a smallest bone density value in the bone density display area.

In addition, according to another embodiment, there is provided a computer program stored in a computer-readable storage medium including instructions that, when executed by a processor, cause the processor to perform operations including overlaying a bone density display area including an implant body placement area with a tooth area, displaying a bone density value corresponding to the bone density display area in a first color, and determining whether to display a second color on an edge of the implant body or an edge of the bone density display area displayed in the first color, based on a bone density difference value between an area having a greatest bone density value and an area having a smallest bone density value in the bone density display area.

Effects

Embodiments have the effect of effective procedure planning by providing bone density information on an implant part when planning an implant procedure.

In addition, embodiments have the effect of planning a more accurate procedure by providing the deviation information of the bone density on an implant part.

In addition, embodiments have the effect of intuitively showing information to a user by displaying the bone density information and bone density deviation information on an implant part in colors.

BEST MODE FOR CARRYING OUT THE INVENTION

Hereinafter, examples are described in detail with reference to the accompanying drawings.

Figure 1:
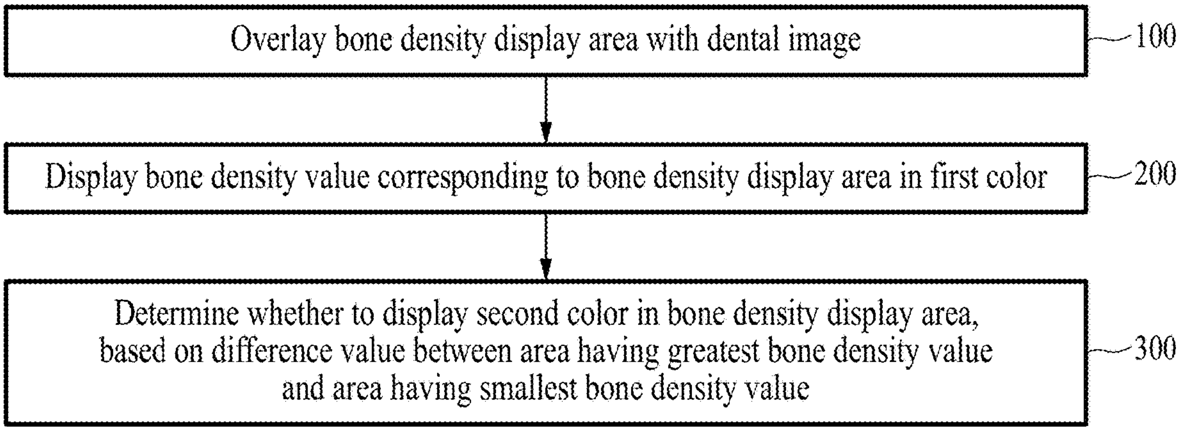
FIG. 1 is a flowchart illustrating a multiple bone density display method according to an embodiment.
Figure 2:
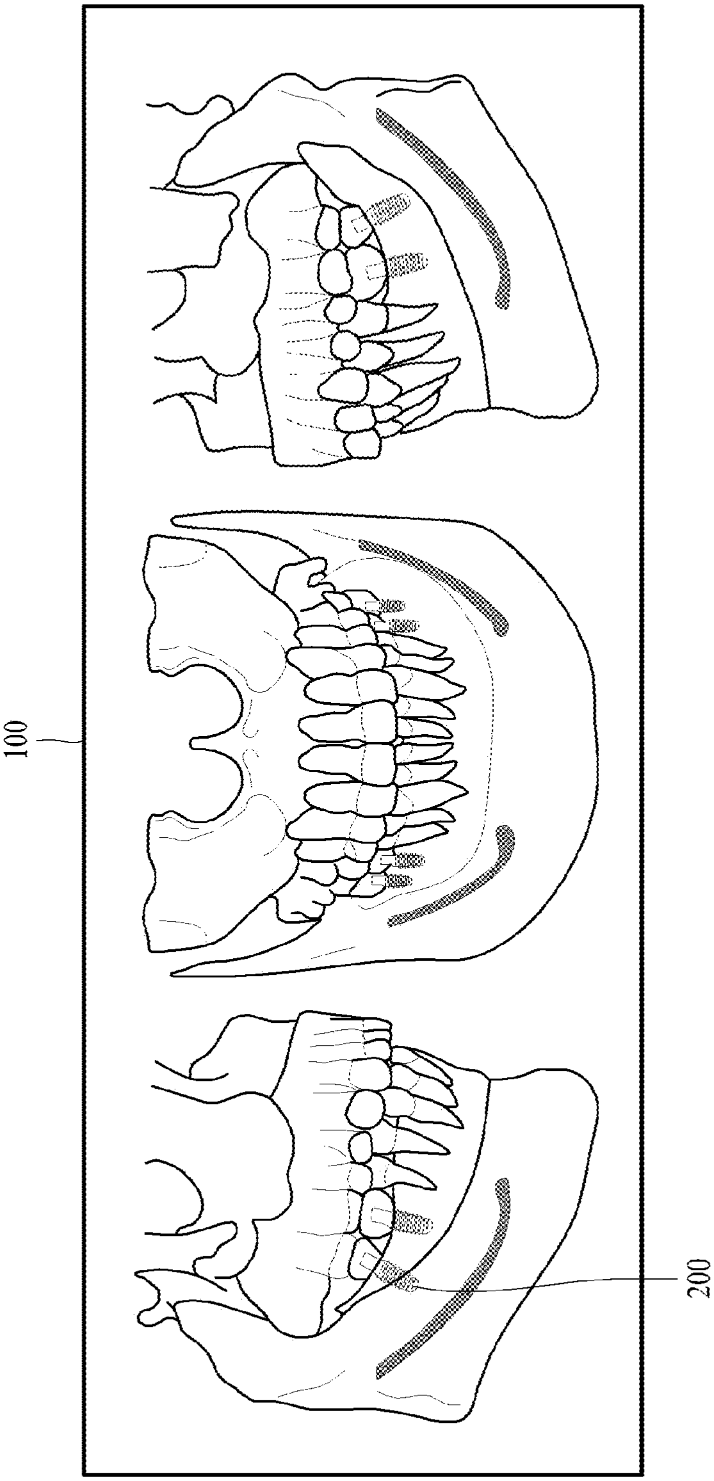
FIG. 2 is a diagram illustrating a dental image screen of a placed implant body, according to an embodiment.
Figure 3:
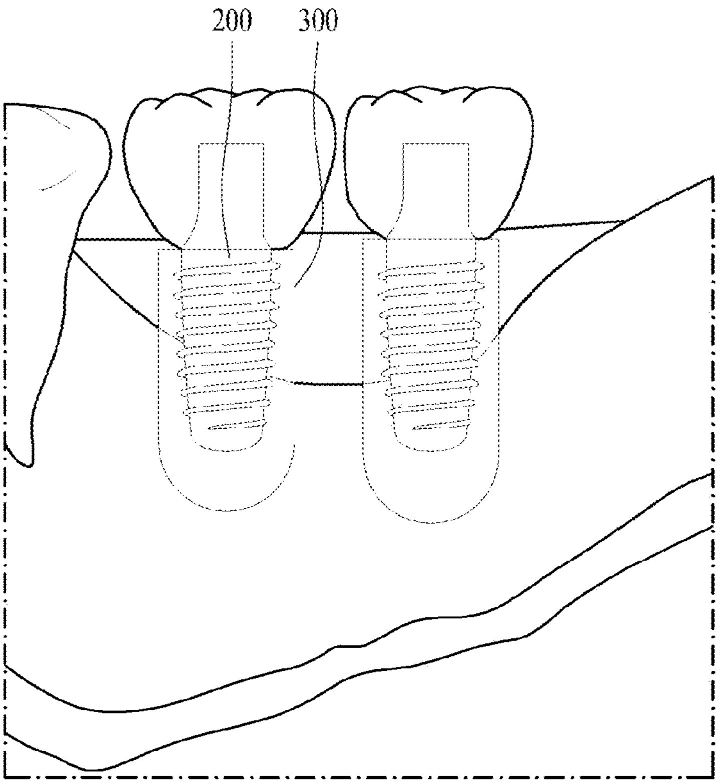
FIG. 3 is a diagram illustrating a bone density display area in an implant body, according to an embodiment.
Figure 4:
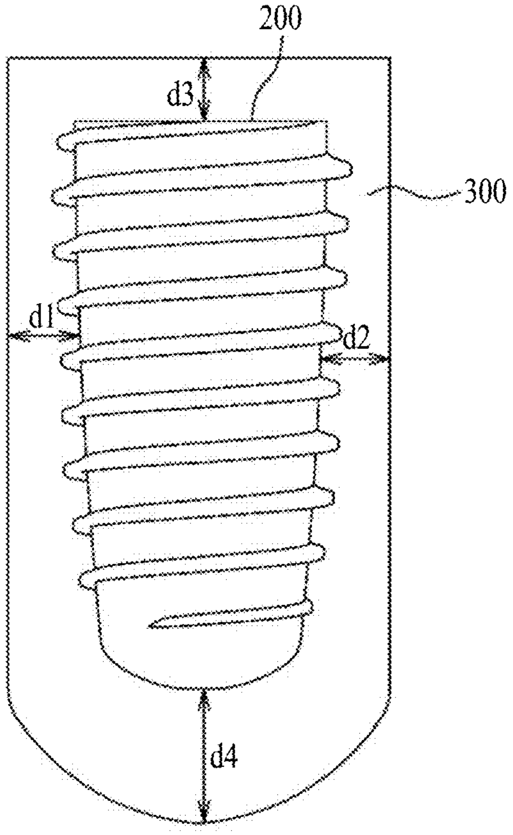
FIG. 4 is a diagram illustrating a distance between an implant body and a bone density display area, according to an embodiment.
Figure 5:
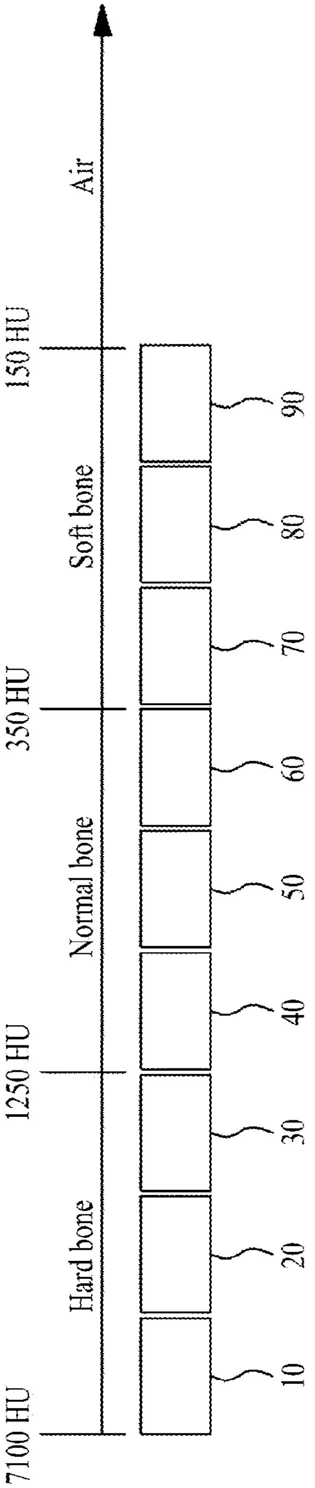
FIG. 5 is a diagram illustrating a bone density grade according to an embodiment.
Figure 6:
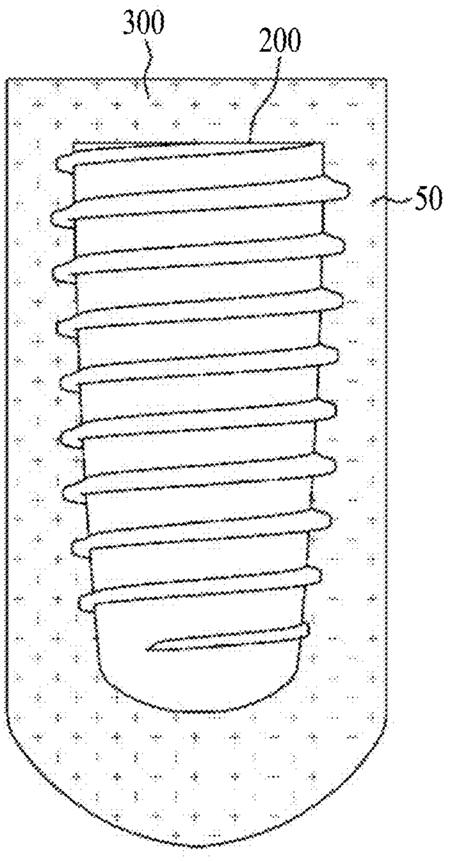
FIG. 6 is a diagram illustrating a color in a bone density display area, according to an embodiment.
Figure 7:
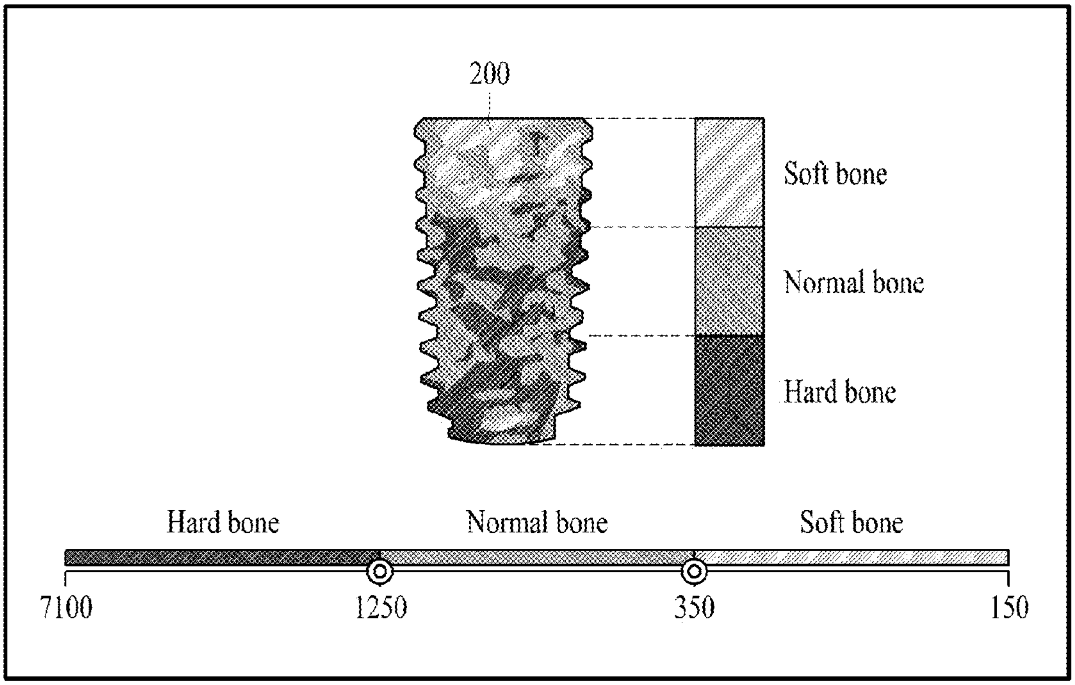
FIG. 7 is a diagram illustrating a combination of at least one color based on bone density corresponding to each pixel of a bone density display area, according to an embodiment.
Figure 8:
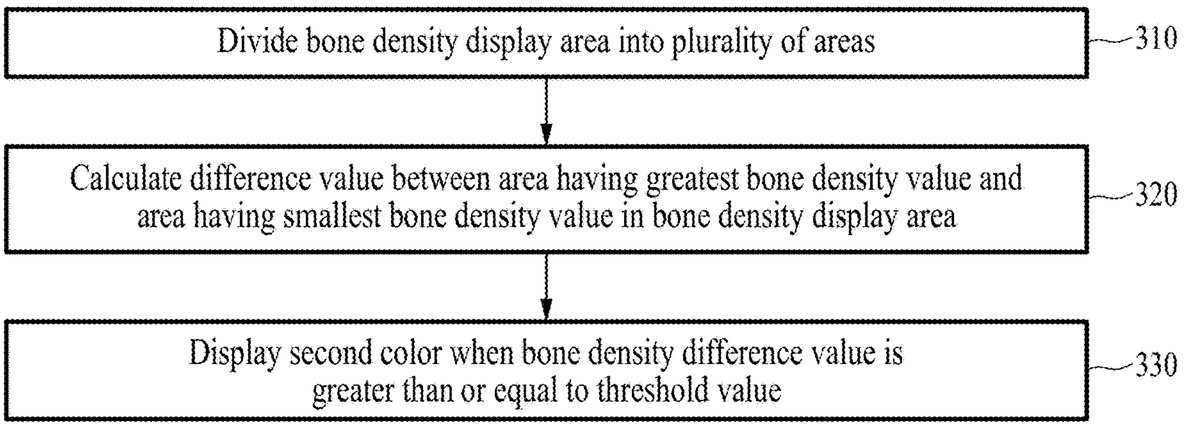
FIG. 8 is a flowchart illustrating a method of displaying a second color in a bone density display area, according to an embodiment.
Figure 9:
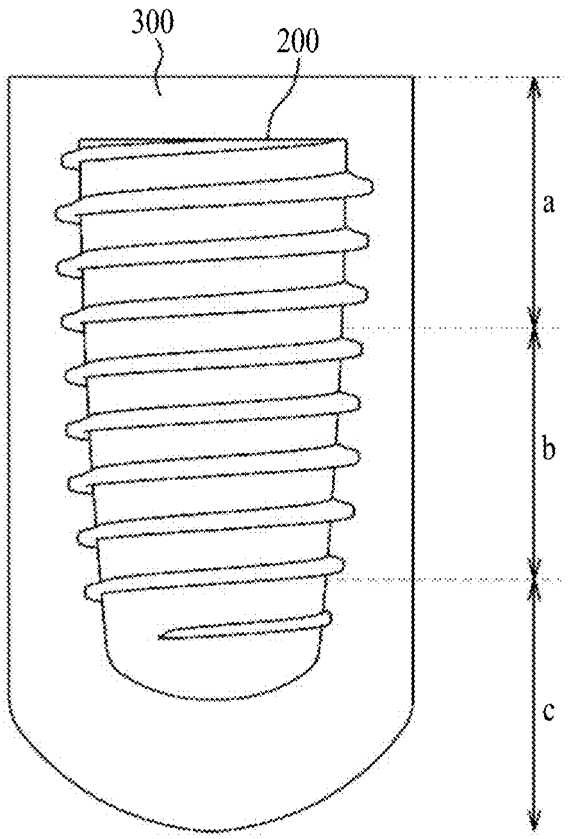
FIGS. 9 to 11 each are diagrams illustrating a method of displaying a second color in a bone density display area, according to an embodiment.
Figure 10:
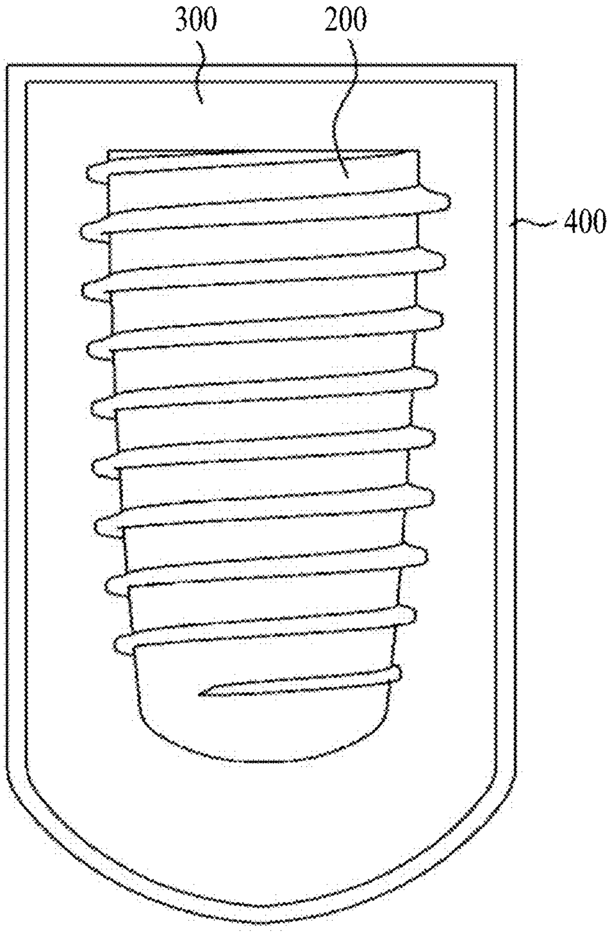
Figure 11:
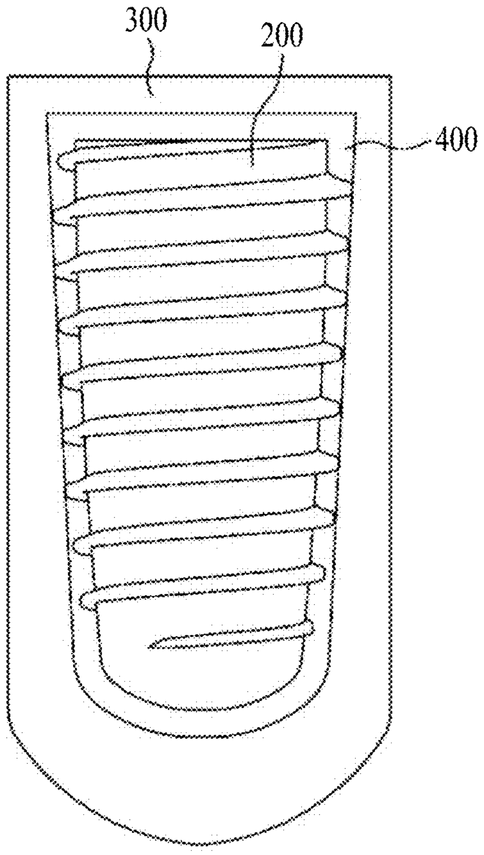
Figure 12:
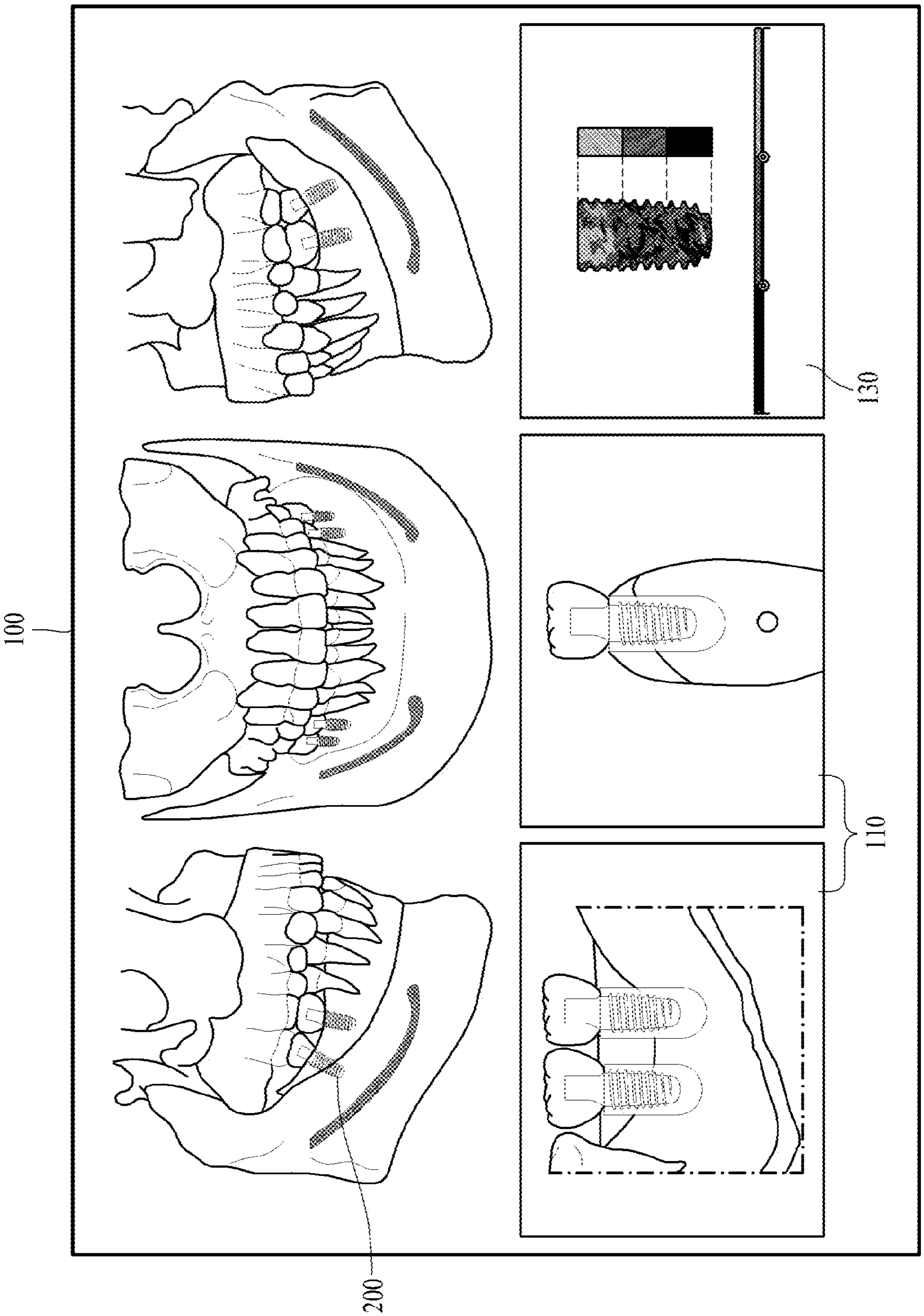
FIG. 12 is a diagram illustrating a final screen provided to a user, according to an embodiment.

FIG. 1 is a flowchart illustrating a multiple bone density display method according to an embodiment; FIG. 2 is a diagram illustrating a dental image screen of a placed implant body, according to an embodiment; FIG. 3 is a diagram illustrating a bone density display area in an implant body, according to an embodiment; FIG. 4 is a diagram illustrating a distance between an implant body and a bone density display area, according to an embodiment; FIG. 5 is a diagram illustrating a bone density grade according to an embodiment; FIG. 6 is a diagram illustrating a color in a bone density display area, according to an embodiment; FIG. 7 is a diagram illustrating a combination of at least one color based on bone density corresponding to each pixel of a bone density display area, according to an embodiment; FIG. 8 is a flowchart illustrating a method of displaying a second color in a bone density display area, according to an embodiment; FIGS. 9 to 11 each are diagrams illustrating a method of displaying a second color in a bone density display area, according to an embodiment; and FIG. 12 is a diagram illustrating a final screen provided to a user, according to an embodiment.

Referring to FIG. 1, the multiple bone density display method according to an embodiment may include operation 100 of overlaying a bone density display area with a dental image, operation 200 of displaying a bone density value corresponding to the bone density display area in a first color, and operation 300 of determining whether to display a second color in the bone density display area, based on a difference value between an area having the greatest bone density value and an area having the smallest bone density value. This multiple bone density display method may be performed by a multiple bone density display device.

In operation 100, the multiple bone density display device may obtain the dental image from a patient's computed tomography (CT) data and oral cavity model data. The dental image may be a 3-dimensional (3D) image. As illustrated in FIG. 2, the placement of a virtual implant body 200 may be displayed in a dental image 100 obtained to establish an implant procedure plan. A virtual implant body may be displayed manually or automatically upon the execution of a program.

As illustrated in FIG. 3, the multiple bone density display device may set a bone density display area 300 to obtain bone density information around the implant body 200. The shape of the bone density display area 300 may be polygonal or elliptical, but the shape is not limited thereto.

The multiple bone density display device may display the set bone density display area 300 overlaid with the implant body 200, and the bone density display area 300 in a translucent state may be overlaid with the implant body 200.

In this case, the bone density display area 300 may include an implant body placement area. The implant body placement area may be an area where an implant body is placed. The implant body placement area may be manually set by a user or may be automatically set based on implant body information including the length and diameter of the implant body.

As illustrated in FIG. 4, the bone density display area 300 may be spaced apart from the boundary of the implant body 200 at a preset distance. For example, a distance d1 between the bone density display area 300 and the left boundary of the implant body 200 may be 1.2 millimeters (mm) to 1.8 mm. In addition, a distance d2 between the bone density display area 300 and the right boundary of the implant body 200 may be 1.2 mm to 1.8 mm. In addition, a distance d3 between the bone density display area 300 and the upper side boundary of the implant body 200 may be 1.2 mm to 1.8 mm. In addition, a distance d4 between the bone density display area 300 and the lower side boundary of the implant body 200 may be 1.7 mm to 2.3 mm, but distances are not limited to the foregoing examples.

Returning to FIG. 1, in operation 200, the multiple bone density display device may perform an operation of displaying the first color in the bone density display area 300. The first color may refer to a bone density value. Bone density may be calculated based on the Hounsfield Unit (hereinafter, 'HU'). The bone density value disclosed in embodiments may refer to an average value of bone density corresponding to all pixels included in the bone density display area.

The multiple bone density display device may determine the first color according to a bone density grade. The bone density grade may be determined based on bone density corresponding to each pixel included in the implant body placement area. More specifically, the multiple bone density display device may calculate a bone density average value for the bone density of all pixels included in the implant body placement area and may determine the first color based on the calculated bone density average value.

The bone density grade may be determined based on the bone density value in the bone density display area 300. As illustrated in FIG. 5, the bone density grade may be determined based on bone quality, and the bone quality may be mainly classified into a hard bone, a normal bone, and a soft bone. The hard bone may have a value between 1250 HU to 7100 HU, the normal bone may have a value between 350 HU to 1250 HU, and the soft bone may have a value between 150 HU to 350 HU.

The hard bone may include a first hard bone 10, a second hard bone 20, and a third hard bone 30. The first hard bone 10, the second hard bone 20, and the third hard bone 30 may each have a random range between 1250 HU to 7100 HU. For example, the first hard bone 10 may have a value between 5150 HU to 7100 HU, the second hard bone 20 may have a value between 3200 HU to 5150 HU, and the third hard bone 30 may have a value between 1250 HU to 3200 HU. However, the values in these ranges are not limited to the foregoing examples and may be adjusted by a user.

The normal bone may include a first normal bone 40, a second normal bone 50, and a third normal bone 60. The first normal bone 40, the second normal bone 50, and the third normal bone 60 may each have a random range between 350 HU to 1250 HU. For example, the first normal bone 40 may have a value between 950 HU to 1250 HU, the second normal bone 50 may have a value between 650 HU to 950 HU, and the third normal bone 60 may have a value between 350 HU to 650 HU. However, the values in these ranges are not limited to the foregoing examples and may be adjusted by a user.

The soft bone may include a first soft bone 70, a second soft bone 80, and a third soft bone 90. The first soft bone 70, the second soft bone 80, and the third soft bone 90 may each have a random range between 150 HU to 350 HU. For example, the first soft bone 70 may have a value between 282 HU to 350 HU, the second soft bone 80 may have a value between 216 HU to 282 HU, and the third soft bone 90 may have a value between 150 HU to 216 HU. However, the values in these ranges are not limited to the foregoing examples and may be adjusted by a user.

The multiple bone density display device may display the bone density grade based on a red, green, and blue (RGB) method. For example, the hard bone may be displayed in blue. The first hard bone 10 may be displayed in dark blue, the second hard bone 20 may be displayed in normal blue, and the third hard bone 30 may be displayed in light blue. The normal bone may be displayed in green. The first normal bone 40 may be displayed in dark green, the second normal bone 50 may be displayed in normal green, and the third normal bone 60 may be displayed in light green. The soft bone may be displayed in red. The first soft bone 70 may be displayed in dark red, the second soft bone 80 may be displayed in normal red, and the third soft bone 90 may be displayed in light red. The colors of the bone density grade are not limited to the foregoing examples and may be randomly selected by a user through a selection button on a screen.

FIG. 6 is a diagram illustrating the result of displaying the first color in the bone density display area 300, according to an embodiment. For example, when the average value of bone density for all pixels included in the bone density display area 300 is 800 HU, the multiple bone density display device may display the bone density display area 300 in normal green corresponding to the second normal bone 50.

On the other hand, instead of displaying the bone density display area 300 in one color according to the average value of bone density as illustrated in FIG. 6, the multiple bone density display device may display the bone density display area 300 with a combination of at least one color according to bone density for each pixel as illustrated in FIG. 7. In other words, the multiple bone density display device may display the bone density display area 300 in a blue system corresponding to the hard bone as the bone density for each pixel increases and may display the bone density display area 300 in a red system corresponding to the soft bone as the bone density for each pixel decreases.

As such, the multiple bone density display device may intuitively provide bone density information of an area that a user intends to see by displaying the bone density display area 300 in a color according to the bone density value.

In addition, when displaying the bone density display area 300 in only one color according to the average value of bone density as illustrated in FIG. 6, a bone density deviation in the bone density display area 300 may not be identified. This bone density deviation may be caused by osteoporosis, accidental bone loss, congenital bone imbalance, or the like, and thus may be critical information for some patients.

Accordingly, when performing drilling on these patients based only on the average value of bone density without considering the bone density deviation in the bone density display area 300, an implant body may not be fixed to a tooth or the implant body may press the tooth during an actual implant procedure, and a bone of these patients may be damaged.

Accordingly, the multiple bone density display device may provide a user with the information using the bone density deviation in the bone density display area 300.

Returning to FIG. 1, in operation 300, the multiple bone density display device may determine whether to display the second color in the bone density display area 300 by considering the bone density deviation in the bone density display area 300. The second color may be determined based on a difference value between an area having the greatest bone density value and an area having the smallest bone density value in the bone density display area 300. In this case, the second color may be different from the first color. The second color may be greatly different in brightness from the first color.

As illustrated in FIG. 8, in more detail, operation 300 of determining whether to display the second color may include operation 310 of dividing the bone density display area 300 into a plurality of areas, operation 320 of calculating a difference value between the area having the greatest bone density value and the area having the smallest bone density value in the bone density display area 300, and operation 330 of displaying the second color when the bone density difference value is greater than or equal to a threshold value.

As illustrated in FIG. 9, the multiple bone density display device may divide the bone density display area 300 into the plurality of areas in a longitudinal direction of the implant body. Since the bone density is greatly different between in an area near a maxillary sinus or a mandibular sinus and an area close to a tooth, an area may be divided into a plurality of areas in a longitudinal direction of the implant body 200; however, a criterion of dividing the area is not limited thereto.

A first area a may be an area close to a tooth, a third area c may be an area close to a mandibular sinus, and a second area b may be an area between the first area a and the third area c.

As described above, when the bone density display area 300 is divided into the first area a, the second area b, and the third area c, the multiple bone density display device may calculate a bone density value by using an average value of bone density of the first area a, a bone density value by using an average value of bone density of the second area b, and a bone density value by using an average value of bond density of the third area c. For example, referring to FIG. 7, the first area a and the second area b may each have the bone density values corresponding to the normal bone, and the third area c may have the bone density value corresponding to the hard bone.

The multiple bone density display device may calculate a bone density difference value between an area having the greatest bone density value and an area having the smallest bone density value among the first area a, the second area b, and the third area c. For example, when the area having the greatest bone density value is the third area c, and the area having the smallest bone density value is the first area a, the multiple bone density display device may calculate a difference between the bone density value of the third area c and the bone density value of the first area a.

The multiple bone density display device may determine whether the bone density deviation in the bone density display area 300 is great or small by comparing the calculated bone density difference value with a preset threshold value. For example, the multiple bone density display device may determine that the bone density deviation in the bone density display area 300 is great when the calculated bone density difference value is greater than or equal to the preset threshold value and may display the second color in the bone density display area 300 such that the determination is identifiable. For example, as illustrated in FIG. 10, the multiple bone density display device may display the second color in an edge area 400 of the first color displayed in the bone density display area 300 when determining that the bone density deviation in the bone density display area 300 is great.

On the other hand, when determining that the bone density deviation in the bone density display area 300 is great, the multiple bone density display area may display the second color in the edge area 400 of the implant body 200 as illustrated in FIG. 11. In other words, the edge area 400 in which the second color is displayed may be between the implant body 200 and the bone density display area 300.

Alternatively, when displaying a bone density value in the implant body 200 with a combination of at least one color according to the bone density corresponding to each pixel, the multiple bone density display device may display the second color on an edge of the implant body 200 without displaying the bone density display area 300.

Accordingly, a user may change the size of a hole for a drilling procedure by considering the second color displayed on a screen even though the bone density grade is classified into the normal bone based on the bone density value in the bone density display area 300 through the first color displayed on the screen.

As illustrated in FIG. 12, the dental image 100 including the implant body 200, which is selected by a user, being placed may be displayed on a screen provided to the user. In addition, an image 110 including the bone density display area 300 displayed in the first color may be displayed on the screen. In addition, an image 130 including the bone density display area 300 displayed with a combination of at least one color according to bone density for each pixel may be displayed on the screen.

Alternatively, an image displaying the second color determined based on the bone density deviation in the bone density display area 300 may be displayed on the screen.

Although the example of displaying the bone density deviation information by displaying the second color on the screen is provided above, the method of providing the bone density deviation information is not limited thereto, and a notification of the bone density deviation information may be displayed on the screen by using numbers, characters, or figures.

Figure 13:
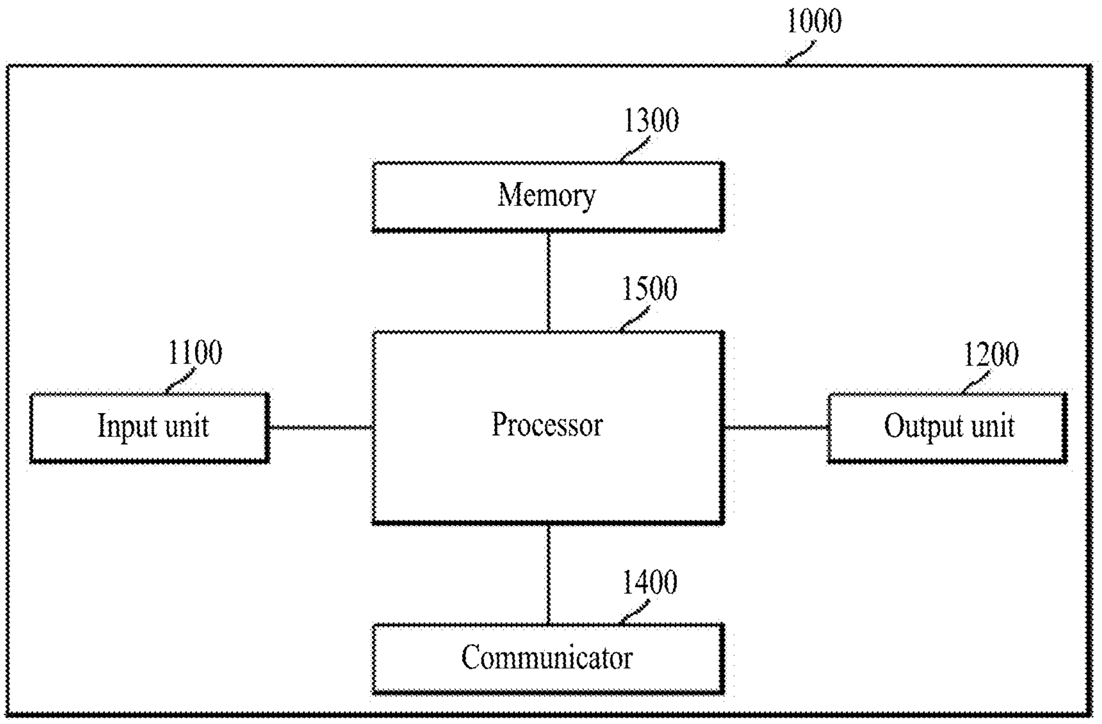
FIG. 13 is a block diagram illustrating a multiple bone density display device according to an embodiment.

FIG. 13 is a block diagram illustrating a multiple bone density display device according to an embodiment.

Referring to FIG. 13, a multiple bone density display device 1000 may include an input unit 1100, an output unit 1200, a memory 1300, a communicator 1400, and a processor 1500.

The input unit 1100 may include at least one input face for receiving selection information of a user. The input unit 1100 may receive the selection information of the user through area designation through mouse dragging or a click state of a mouse from the user.

In addition, the input unit 1100 may include at least one of a communicator for receiving multiple bone density display information and state information of a patient by wire or wirelessly and an input face, such as a keyboard or a microphone, for receiving an input of a search word or sentence.

In addition, the input unit 1100 may receive an input of a manipulation signal for entering an automatic bone density display mode (Fixture) or a manual bone density display mode (Manual).

The output unit 1200 may display a program screen including pieces of information generated by the processor 1500.

The output unit 1200 may output screens corresponding to information input based on information input from the input unit 1100. The output unit 1200 may output dental images of a placed implant body, images where an implant body is viewed from various directions, and images displaying a color for a bone density value and a bone density deviation value in a bone density display area.

The output unit 1200 may display a user interface for entering the automatic bone density display mode or the manual bone density display mode on a screen. When entering to a bone density display mode, a user interface for selecting a bone density mode, a view mode, or other modes may be displayed on the screen.

When selecting the bone density mode, a bone density value or a color map may be displayed. When selecting the view mode, bone density may be displayed in one of an axial view, a frontal plane view, and a sagittal plane view. In addition, when selecting a multimode, bone density may be displayed through multiple consecutive cross-sectional images.

The memory 1300 may store pieces of data for a multiple bone density display control program or other general operations. Specifically, the memory 1300 may store the pieces of data and instructions for multiple application programs driven in the multiple bone density display device and operations of the multiple bone density display device 1000.

The memory 1300 may store dental image data of a patient. The dental image data may include X-ray data, CT data, or oral cavity model data, but examples are not limited thereto.

The memory 1300 may include magnetic storage media or flash storage media, but examples are not limited thereto.

The communicator 1400 may be a device including hardware and software for transmitting or receiving a signal, such as a control signal or a data signal, through a wired or wireless connection to another network device.

The communicator 1400 may transmit or receive a screen displaying pieces of multiple bone density information and pieces of patient information.

The communicator 1400 may perform communication by using a low power wireless network (LPWN) and a low power wide area network (LPWAN), including NB-IoT, LoRa, SigFox, or LTE-CATI, besides 3G, LTE, and 5G.

The communicator 1400 may perform communication by using a communication method using a wireless local area network (LAN), such as WiFi 80211a/b/g/n, besides a wired LAN. In addition, the communicator 1400 may perform communication with a microwave or other external devices by using near field communication (NFC), Bluetooth, or other communication methods.

In this case, the communicator 1400 is not an essential component of the multiple bone density display device 1000 and may be mounted or unmounted on the multiple bone density display device 1000.

The processor 1500 may be a kind of central processing unit (CPU) and may control the general operation of the multiple bone density display device.

The processor 1500 may include all types of devices for processing data. In this case, the 'processor' may refer to, for example, a data processing device embedded in hardware and having a physically structured circuit to perform functions expressed in code or instructions included in a program. Likewise, the examples of the data processing device embedded in hardware may include a microprocessor, a CPU, a processor core, a multiprocessor, an application-specific integrated circuit (ASIC), a field programmable gate array (FPGA), or the like, but examples are not limited thereto.

The processor 1500 may perform the following operations.

The processor 1500 may execute a multiple bone density control program. Specifically, when placing an implant body for an implant procedure, the bone density display mode may be performed according to a user manipulation signal input from the input unit 1100.

The processor 1500 may provide the screen information of a dental image displaying a bone density display area preset based on information input from a user to the output unit 1200.

The processor 1500 may calculate a bone density value by calculating an average value of HU of the bone density display area to display color information.

The processor 1500 may control to display a first color in the bone density display area corresponding to a bone density grade based on the calculated bone density value.

The processor 1500 may provide the output unit 1200 with the screen displaying a second color in the bone density display area.

For this, the processor 1500 may divide the bone density display area into a plurality of areas and may calculate a bone density value corresponding to each area. The processor 1500 may calculate a difference value between an area having the greatest bone density value and an area having the smallest bone density value in the bone density display area. The processor 1500 may control to display the second color in the bone density display area based on the bone density difference value. For example, when the bone density difference value is greater than or equal to a threshold value, the processor 1500 may control to display the second color in the bone density display area.

The processor 1500 may provide the output unit 1200 with a final screen displaying colors in a dental image, an implant body, a bone density display area, a bone density value, and a bone density deviation.

Various embodiments as set forth herein may be implemented as software (e.g., a program) including instructions stored in a storage medium (e.g., a memory (an internal memory or an external memory)) readable by a machine (e.g., a computer). The machine may be a device for calling the stored instructions from the storage medium and performing operations according to the called instructions and may include an electronic device according to the disclosed embodiments. When a controller executes the instructions, the controller may perform functions corresponding to the instructions directly by itself or by controlling other components. The instructions may include code generated or executed by a compiler or an interpreter. The machine-readable storage medium may be provided in the form of a non-transitory storage medium. Here, the term "non-transitory" simply means that the storage medium is a tangible device and does not include a signal, and the term does not distinguish whether data is semi-permanently or temporarily stored in the storage medium.

According to an embodiment, a method according to various embodiments of the disclosure may be included and provided in a computer program product.

According to an embodiment, a computer-readable storage medium storing a computer program may include instructions that cause a processor to perform operations including overlaying a bone density display area including an implant body placement area with a tooth area, displaying a bone density value corresponding to the bone density display area in a first color, and determining whether to display a second color on an edge of the implant body or an edge of the bone density display area displayed in the first color, based on a bone density difference value between an area having a greatest bone density value and an area having a smallest bone density value in the bone density display area.

According to an embodiment, a computer program stored in a computer-readable storage medium may include instructions that cause a processor to perform operations including overlaying a bone density display area including an implant body placement area with a tooth area, displaying a bone density value corresponding to the bone density display area in a first color, and determining whether to display a second color on an edge of the implant body or an edge of the bone density display area displayed in the first color, based on a bone density difference value between an area having a greatest bone density value and an area having a smallest bone density value in the bone density display area.

Although described above with reference to the drawings and embodiments, it could be understood by those skilled in the art that the embodiments may be modified and changed in various manners within the scope without departing from the technical goals of embodiments disclosed in the scope of the claims below.

The invention claimed is:

1. A method of displaying multiple bone density densities performed in a multiple bone density display device when planning an implant procedure, the method comprising:

overlaying a bone density display area comprising an implant body placement area with a tooth area;

displaying a first color in the bone density display area, wherein the first color refers to a bone density value corresponding to the bone density display area;

dividing the bone density display area into a plurality of areas in a longitudinal direction of an implant body;

calculating a bone density difference value between an area having a greatest bone density value and an area having a smallest bone density value among the plurality of areas;

comparing the calculated bone density difference value with a preset threshold value, determining that the bone density difference value is greater than or equal to the preset threshold value, and displaying a second color on an edge of the implant body or an edge of the bone density display area in response to the determination that the bone density difference value is greater than or equal to the preset threshold value, thereby allowing implant procedures.

2. The method of claim 1, wherein the displaying of the second color comprises displaying the second color on the edge of the bone density display area in response to the determination that the bone density difference value is greater than or equal to the preset threshold value.

3. The method of claim 1, wherein the area having the greatest bone density value comprises an area adjacent to a maxillary sinus or a mandibular sinus, and the area having the smallest bone density value comprises an area adjacent to a tooth.

4. The method of claim 1, wherein the displaying the first color comprises:

determining a bone density grade based on a bone density value of each pixel comprised in the implant body placement area; and determining the first color according to the bone density grade, wherein the bone density grade comprises a first hard bone, a second hard bone, and a third hard bone, a first normal bone, a second normal bone, and a third normal bone, and a first soft bone, a second soft bone, and a third soft bone.

5. The method of claim 1, wherein the implant body placement area is automatically set based on implant body information comprising a length and diameter of the implant body.

6. A multiple bone density display device comprising:

a memory configured to store a control program for displaying multiple bone density densities; and a processor configured to execute the control program stored in the memory, wherein the processor is further configured to overlay a bone density display area comprising an implant body placement area with a tooth area, display a first color in the bone density display area, wherein the first color refers to a bone density value corresponding to the bone density display area, divide the bone density display area into a plurality of areas in a longitudinal direction of an implant body, calculate a bone density difference value between an area having a greatest bone density value and an area having a smallest bone density value among the plurality of areas, compare the calculated bone density difference value with a preset threshold value, determine that the bone density difference value is greater than or equal to the preset threshold value, and display a second color on an edge of the implant body or an edge of the bone density display area in response to the determination that the bone density difference value is greater than or equal to the preset threshold value, thereby allowing implant procedures.

7. The multiple bone density display device of claim 6, wherein the processor is further configured to display the second color on the edge of the bone density display area when the bone density difference value is greater than or equal to the preset threshold value.

8. The multiple bone density display device of claim 6, wherein the area having the greatest bone density value comprises an area adjacent to a maxillary sinus or a mandibular sinus, and the area having the smallest bone density value comprises an area adjacent to a tooth.

9. The multiple bone density display device of claim 6, wherein the processor is further configured to control the implant body placement area to be automatically set based on implant body information comprising a length and diameter of the implant body.

10. A non-transitory computer-readable storage medium storing a computer program comprising instructions that, when executed by a processor, cause the processor to perform operations comprising:

overlaying a bone density display area comprising an implant body placement area with a tooth area;

displaying a first color in the bone density display area, wherein the first color refers to a bone density value corresponding to the bone density display area;

dividing the bone density display area into a plurality of areas in a longitudinal direction of an implant body;

calculating a bone density difference value between an area having a greatest bone density value and an area having a smallest bone density value among the plurality of areas;

comparing the calculated bone density difference value with a preset threshold value, determining that the bone density difference value is greater than or equal to the preset threshold value, and displaying a second color on an edge of the implant body or an edge of the bone density display area in response to the determination that the bone density difference value is greater than or equal to the preset threshold value, thereby allowing implant procedures.

* * * * *